United States Patent [19]

Cavero et al.

[11] Patent Number: 5,426,117
[45] Date of Patent: Jun. 20, 1995

[54] N-METHYL-2-(3-PYRIDYL)-TETRAHYDROTHIO-PYRAN-2-CARBOTHIOAMIDE 1-OXIDE TO THE PREPARATION OF MEDICINAL PRODUCTS INTENDED FOR TREATMENT OF CORONARY INSUFFICIENCY

[75] Inventors: Icilio Cavero, Creteil; Serge Mondot, Cagnes Sur Mer, both of France

[73] Assignee: Rhone-Poulenc Sante, Antony Cedex, France

[21] Appl. No.: 13,549

[22] Filed: Feb. 4, 1993

Related U.S. Application Data

[63] Continuation of Ser. No. 785,148, Oct. 29, 1991, abandoned, which is a continuation of Ser. No. 607,408, Oct. 31, 1990, abandoned.

[30] Foreign Application Priority Data

Oct. 31, 1989 [FR] France ................ 89 14272

[51] Int. Cl.$^6$ .............................................. A61K 31/44
[52] U.S. Cl. ................................. 514/336; 514/314
[58] Field of Search ............................ 514/314, 336

[56] References Cited

U.S. PATENT DOCUMENTS 4,568,682 2/1986 Aloup et al. ................ 514/336
4,751,234 6/1988 Aloup et al. ................ 514/314

FOREIGN PATENT DOCUMENTS 0097584 1/1984 European Pat. Off. ... C07D 409/04
323745 12/1988 European Pat. Off. .

OTHER PUBLICATIONS

"RP 49356 is a Potent Opener of ATP-Modulated Potassium Channels in Cardiac Myocytes", Br. J. Pharmacol., vol. 95, Suppl., 1988, p. 814P, D. Escande et al.
European Search Report dated Jul. 10, 1990, FR 8914272, FA 433968 "Potassium Channel Operners Act Through an Activation of ATP-sensitive K+-ATP Channels in Cardiac Myocytes", Escande et al., Pflugers Arch. Eur. J. Physiol vol. 414, No. 6, Sep. 1989, pp. 669-675.
"The potassium channel opener RP 49356 modifies the ATP-sensitivity of K+-ATP channels in Cardiac Myocytes", Pflugers Arch. Eur. J. Physiol., vol. 414, Suppl. 1, 1989, p. 175, Springer Verlag, D. Thuringer, et al.
"Effects of Ca2+ antagonists of K+-channel activators on K+-induced contractions in the rat aorta", Lawson et al., J. Auton. Pharmac., vol. 9, No. 5, Oct. 1989, pp. 329-336.

Primary Examiner—Raymond Henley, III
Assistant Examiner—Minna Moezie
Attorney, Agent, or Firm—Morgan & Finnegan

[57] ABSTRACT

Application of N-Methyl-2-(3-pyridyl)tetrahydrothiopyran-2-carbothioamide 1-oxide, in the form of a racemic mixture of the 1S,2S and 1R,2R isomers or in the form of the 1R,2R isomer, to the preparation of a medicinal product intended for the treatment of coronary insufficiency.

10 Claims, No Drawings

N-METHYL-2-(3-PYRIDYL)-TETRAHYDROTHIO-PYRAN-2-CARBOTHIOAMIDE 1-OXIDE TO THE PREPARATION OF MEDICINAL PRODUCTS INTENDED FOR TREATMENT OF CORONARY INSUFFICIENCY

This is a continuation of application Ser. No. 07/785,148, filed on Oct. 29, 1991, now abandoned which is a continuation of application of Ser. No. 07/607,408, filed on Oct. 31, 1990, now abandoned.

FIELD OF THE INVENTION

The present invention relates to the application of 2-(3-pyridyl)tetrahydrothiopyran-2-carbothioamide 1-oxide to the preparation of vascular muscle-relaxant medicinal products which are especially useful in the treatment of coronary insufficiency and as a cardio protective agent.

BACKGROUND OF THE INVENTION

In European Patent No. EP 97,584, thioformamide derivatives of general formulas

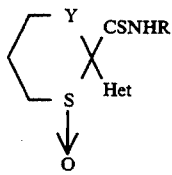

(I)

in which R represents a hydrogen atom or an alkyl radical containing 1 to 4 carbon atoms, Her represents a heterocyclic radical aromatic in nature and Y represents a valency bond or a methylene radical, and which exhibit exceptional antihypertensive properties, have been described.

DETAILED DESCRIPTION OF THE INVENTION

It has now been found, and this forms the subject of the present invention, that N-methyl-2-(3-pyridyl)tetrahydrothiopyran-2-carbothioamide 1-oxide, in the form of a mixture of its transisomers which may be represented in the following manner:

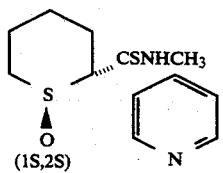

(II)

and

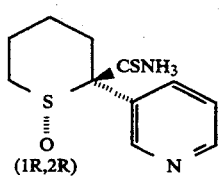

(III)

and the isomer (III) whose absolute configuration is 1R,2R, exhibit advantageous coronary dilator properties.

The subject of the present invention is hence the application of a mixture of the isomers (II) and (III) or of the isomer (III) of N-methyl-2-(3-pyridyl)tetrahydro-thiopyran-2-carbothioamide 1-oxide to the preparation of medicinal products having a vascular muscle-relaxant action which are especially useful as protective agents with respect to myocardial ischaemia, in particular in the treatment of angina pectoris.

EXPERIMENTATION

The effect of the mixture of the products of formulae (II) and (III) (racemic mixture) and of the product of formula (III) on the coronary arterial circulation may be demonstrated in the following manners Male or female Beagle dogs weighing between 14 and 18 kg are anaesthetized with pentobarbital sodium (35 mg/kg i.v. followed by a continuous perfusion of 3 mg/kg/hour at a flow rate of 0.2 cc/minute).

The animals are intubated with an endotracheal probe and placed under artificial respiration. A left thoracotomy is performed at the 5th intercostal space and an electromagnetic probe is placed on the origin of the circumflex artery as well as on the aortic arch for recording the coronary arterial flow rate and the cardiac flow rate.

The arterial blood pressure is measured by means of a STATAM P23Id sensor connected to a catheter introduced into the femoral artery. The heart rate is calculated electronically from the pulse wave. A femoral vein is catheterized for injection of the products.

All the parameters are recorded on an 8-track Polygraph (Linearcorder Mark VII) and their values, after digitization are stored in a computer for processing the data.

The test products, dissolved in distilled water, are administered in intravenous perfusion for 15 minutes in a volume and at the rate of 1 cc/minute.

The mixture of the isomers (II) and (III) (racemic mixture) at doses of 2.5 and 5 μg/kg/minute perfused for 15 minutes (total doses administered equal to 37.5 and 75 μg/kg, on the basis of 3 dogs treated per dose) markedly increases the coronary arterial flow rate; the coronary dilator effect reaches its peak effect at the end of perfusion (+49% and +112%, respectively, for initial flow rates of 33±2 and 38±4 cc/minute), and it still persists significantly for approximately 1 hour after the end of the perfusion.

The isomer (III) also brings about a marked and lasting increase in the coronary arterial flow rate, and with a potency of activity approximately twice as high as that of the racemic mixtures at the end of perfusion, at the peak of the effect, an increase in the coronary arterial flow rate of +62% and +103%, respectively, at respective doses of 1 and 2.5 μg/kg (total doses administered equal to 15 and 37.5 μg/kg) is observed.

It is most especially advantageous to note that the coronary dilator effect is accompanied by only a slight acceleration (approximately 10%) in the heart rate, as well as by a very moderate reduction (in the region of 10-12%) in the mean arterial blood pressure. These results, which are collated in Table I, show that these products exert a vascular muscle-relaxant effect which is selective for the coronary arterial bed, since it is not observed at the level of the systemic circulation (absence of hypotension and of any increase in the cardiac flow rate).

TABLE I

EFFECTS ON THE HEART RATE (HR), MEAN ARTERIAL BLOOD PRESSURE (MABP) AND CORONARY ARTERIAL FLOW RATE (CAF) IN PENTOBARBITAL-ANAESTHETIZED DOGS

| Product | Dose 1 g/kg/min i.v. | Parameter | Mean initial value ± SEM | After beginning of i.v. perfusion (minutes) 5 | 10 | 15 | After end of i.v. perfusion (minutes) 5 | 15 | 30 | 60 |
|---|---|---|---|---|---|---|---|---|---|---|
| Racemic mixture of the isomers (II) and (III) | 2.5 | HR | 158 ± 4 | +1 | +3 | +7 | +6 | 0 | 0 | −1 |
| | | MABP | 106 ± 4 | −5 | −9 | −10 | −11 | −11 | −9 | −5 |
| | | CAF | 33 ± 2 | +15 | +41 | +49 | +34 | +12 | +14 | +18 |
| | 5.0 | HR | 155 ± 3 | +3 | +9 | +10 | +6 | +8 | +5 | +2 |
| | | MABP | 100 ± 2 | −4 | −11 | −12 | −12 | −11 | −10 | −8 |
| | | CAF | 38 ± 4 | +49 | +103 | +112 | +86 | +34 | +19 | 0 |
| Isomer III | 1.0 | HR | 149 ± 2 | +3 | +9 | +10 | +11 | +13 | +11 | +11 |
| | | MABP | 115 ± 5 | −1 | 0 | 0 | +1 | +2 | +2 | +8 |
| | | CAF | 39 ± 2 | +15 | +51 | +62 | +43 | +28 | +18 | +18 |
| | 2.5 | HR | 159 ± 3 | +8 | +9 | +10 | +9 | +9 | +3 | +3 |
| | | MABP | 118 ± 7 | +3 | +5 | −10 | −13 | −11 | −11 | −11 |
| | | CAF | 39 ± 2 | +41 | +88 | +103 | +88 | +48 | +38 | +21 |

(a) HR: beats/min
MABP: mmHg
CAF: ml/min

It emerges from this that the racemic mixture of the isomers (II) and (III) and the isomer (III) improve coronary circulation by a direct and specific effect on the arterial bed, without significant modification of cardiac dynamics and, in particular, of arterial blood pressure.

In dogs, at daily oral doses of 0.3 and 1 mg/kg (1 month of treatment), N-methyl-2-(3-pyridyl)tetrahydrothiopyran-2-carbothioamide 1-oxide has shown satisfactory general tolerability.

The racemic mixture of the isomers (II) and (III) and the isomer (III) are useful in the therapy of coronary insufficiency, and they may be used as antianginals and cardio protective agents.

The racemic mixture of the isomers (II) and (III) of N-methyl-2-(3-pyridyl)tetrahydrothiopyran-2-carbothioamide 1-oxide may be prepared under the conditions described in European Patent No. EP 97,584, in which it is designated "Form A" or "the more polar product" [the polarity being determined by thin-layer chromatography (TLC)].

(1R,2R)-N-Methyl-2-(3-pyridyl)tetrahydrothiopyran-2-carbothioamide 1-oxide may be obtained either by resolution of the racemate under the appropriate conditions, or by the action of methyl isothiocyanate on a previously anionized sulphoxide of formula:

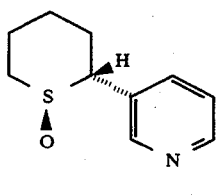

(IV)

or

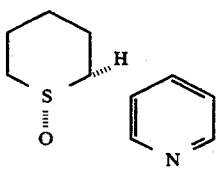

(V)

In general, the reaction is performed by adding a solution of sulphoxide of formula (IV) or (V) or of a mixture of these sulphoxides in an inert organic solvent such as an ether, e.g. tetrahydrofuran, to sodium amide (optionally prepared in situ) in liquid ammonia, working at the boiling point of the reaction mixture, i.e. at −30° C., and then adding a solution of methyl isothiocyanate in an inert organic solvent such as an ether, e.g. tetrahydrofuran, at the same temperature.

Sulphoxides of formula (IV) or (V) or mixtures thereof may be obtained by the stereoselective oxidation of a product of formula:

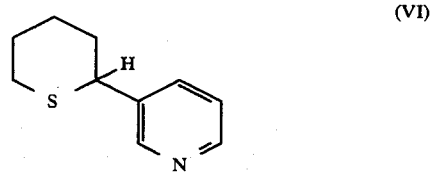

(VI)

either chemically or biochemically.

The selective chemical oxidation is carried out in the presence of an asymmetry inducer such as (+)-(diethyl tartrate) and a titanium (IV) derivative such as a titanium (IV) alcoholate, by means of a hydroperoxide such as cumyl or tert-butyl hydroperoxide. The reaction is generally performed in an organic solvent such as a halogenated aliphatic hydrocarbon (methylene chloride, 1,2-dichloroethane) at a temperature in the region of −20° C.

The selective biochemical oxidation is carried out by means of a culture of a filamentous fungus such as *Aspergillus foetidus* NRRL 337.

The product of formula (VI) may be obtained, e.g., by decarboxylation of the acid of formula:

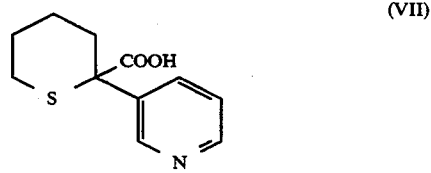

(VII)

by heating to a temperature of between 130° and 160° C., the acid of formula (VII) being obtained under the conditions described in European Patent No. EP 73,704.

The medicinal products improving coronary circulation consist of N-methyl-2-(3-pyridyl)tetrahydrothiopyran-2-carbothioamide 1-oxide in the form of a 1S,2S/1R,2R racemic mixture or in the form of the 1R,2R isomer, in the pure state or in the form of a composition in which they are combined with any other pharmacologically compatible product, which may be inert or physiologically active. These medicinal products may be used orally, intravenously, sublingually and also transdermally.

As solid compositions for oral or sublingual administration, tablets, pills, powders (hard gelatin capsules, wafer capsules) or granules may be used. In these compositions, the active principle is mixed with one or more inert diluents such as starch, cellulose, sucrose, lactose or silica. These compositions can also comprise substances other than diluents, e.g. one or more lubricants such as magnesium stearate or talc, a coloring, a coating (dragees) or varnish.

As liquid compositions for oral administration, pharmaceutically acceptable solutions, suspensions, emulsions, syrups and elixirs containing inert diluents such as water, ethanol, glycerol, vegetable oils or liquid paraffin may be used. These compositions can comprise substances other than diluents, e.g. wetting products, sweeteners, thickeners, flavorings or stabilizers.

The sterile compositions for parenteral administration can preferably be suspensions, emulsions or non-aqueous solutions. As a solvent or vehicle, water, propylene glycol, a polyethylene glycol, vegetable oils especially olive oil, injectable organic esters, e.g. ethyl oleate, or other suitable organic solvents may be employed. These compositions can also contain adjuvants, especially wetting agents, tonicity regulators, emulsifiers, dispersants and stabilizers.

The sterilization maybe carried out in several ways, e.g. by aseptic filtration, by incorporating sterilizing agents in the composition, by irradiation or by heating. They may also be prepared in the form of sterile solid compositions which can be dissolved at the time of use in a sterile injectable medium.

The compositions for transdermal administrations are presented in the form of patches, in which the medicinal product is dispersed in a suitable matrix permitting its gradual release.

In human therapy, N-methyl-2-(3-pyridyl)tetrahydrothiopyran-2-carbothioamide 1-oxide, in the form of a racemic mixture of the 1S,2S and 1R,2R forms or in the form of the 1R,2R isomer, is useful in the treatment of coronary insufficiency and, in particular, in the treatment of angina pectoris. It is also useful as a cardio protective agent against ischaemic attacks.

The doses depend on the effect sought, the period of treatment and the administration route used. For an adult, they are generally between 0.05 and 5 mg per day parenterally and between 1 and 10 mg per day orally. Generally speaking, the doctor will determine the appropriate dosage in accordance with the age and weight and all other factors specific to the subject to be treated.

The examples which follow illustrate pharmaceutical compositions which are usable for the treatment of coronary insufficiency.

EXAMPLE A

Tablets containing a 5 mg dose of active product and having the following composition are prepared according to the usual procedure:

| | |
|---|---|
| N-methyl-2-(3-pyridyl)tetrahydrothiopyran-2-carbothioamide 1-oxide, racemic mixture of 1S,2S and 1R,2R forms | 5 mg |
| Microcrystalline cellulose | 15 mg |
| Lactose | 10 mg |
| Polyoxyethylene glycol 6000 | 5 mg |
| Magnesium stearate | 1 mg |

EXAMPLE B

A solution for intravenous injection having the following composition is prepared according to the usual procedures:

| | |
|---|---|
| (1R,2R)-N-methyl-2-(3-pyridyl)tetrahydrothiopyran-2-carbothioamide 1-oxide | 1 mg |
| Injectable solution | 5 cc |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A method of treating a patient for coronary insufficiency without significantly modifying cardiac dynamics comprising administering to a patient in need of such treatment an effective amount less than 5 mg per day parenterally or less than 10 mg per day orally of N-methyl-2-(3-pyridyl)tetrahydrothiopyran-2-carbothioamide 1-oxide to alleviate coronary insufficiency, in the form of a racemic mixture of the 1S,2S and 1R,2R isomers or in the form of the 1R,2R isomer.

2. A method according to claim 1, wherein the patient is suffering from angina pectoris.

3. A method according to claim 1, wherein the patient is suffering from myocardial ischemia.

4. A method according to claim 1, wherein about 2.5 mg is administered.

5. A method of treating a patient so as to provide a vascular muscle-relaxant action without significantly modifying cardiac dynamics comprising administering to a patient in need of such treatment an effective amount less than 5 mg per day parenterally or less than 10 mg per day orally of N-methyl-2-(3-pyridyl)tetrahydrothiopyran-2-carbothioamide 1-oxide to provide a vascular muscle-relaxant action, in the form of a racemic mixture of the 1S,2S and 1R,2R isomers or in the form of the 1R,2R isomer.

6. A method according to claim 5, wherein about 2.5 mg is administered.

7. A method of treating a patient for coronary insufficiency without significantly modifying cardiac dynamics comprising administering to a patient in need of such treatment about 1 mg of N-methyl-2-(3-pyridyl)tetrahydrothiopyran-2-carbothioamide 1-oxide to alleviate coronary insufficiency, in the form of a racemic mixture of the 1S,2S and 1R,2R isomers or in the form of the 1R,2R isomer.

8. A method of treating a patient so as to provide a vascular muscle-relaxant action without significantly modifying cardiac dynamics comprising administering to a patient in need of such treatment about 1.0 mg of N-methyl-2-(3-pyridyl)tetrahydrothiopyran-2-carbothioamide 1-oxide to provide a vascular muscle-relaxant action, in the form of a racemic mixture of the 1S,2S and 1R,2R isomers or in the form of the 1R,2R isomer.

9. A method of treating a patient for coronary insufficiency without significantly modifying cardiac dynamics comprising administering to a patient in need of such treatment about 2.5 mg of N-methyl-2-(3-pyridyl)tetrahydrothiopyran-2-carbothioamide 1-oxide to alleviate coronary insufficiency, in the form of a racemic mixture of the 1S,2S and 1R,2R isomers or in the form of the 1R,2R isomer.

10. A method of treating a patient so as to provide a vascular muscle-relaxant action without significantly modifying cardiac dynamics comprising administering to a patient in need of such treatment about 2.5 mg of N-methyl-2-(3-pyridyl)tetrahydrothiopyran-2-carbothioamide 1-oxide to provide a vascular muscle-relaxant action, in the form of a racemic mixture of the 1S,2S and 1R,2R isomers or in the form of the 1R,2R isomer.

* * * * *